United States Patent [19]

Lash

[11] Patent Number: 5,531,728

[45] Date of Patent: * Jul. 2, 1996

[54] ABSORBENT STRUCTURES CONTAINING THERMALLY-BONDED STIFFENED FIBERS AND SUPERABSORBENT MATERIAL

[75] Inventor: Glen R. Lash, Cincinnati, Ohio

[73] Assignee: The Procter & Gamble Company, Cincinnati, Ohio

[ * ] Notice: The term of this patent shall not extend beyond the expiration date of Pat. No. 5,217,445.

[21] Appl. No.: 332,238

[22] Filed: Oct. 31, 1994

Related U.S. Application Data

[63] Continuation of Ser. No. 625,776, Dec. 17, 1990, Pat. No. 5,360,420, which is a continuation-in-part of Ser. No. 468,549, Jan. 23, 1990, abandoned.

[51] Int. Cl.$^6$ .................................................. A61F 13/20
[52] U.S. Cl. ........................ 604/378; 604/365; 604/366; 604/374
[58] Field of Search ..................................... 604/365–378

[56] References Cited

U.S. PATENT DOCUMENTS

| | | | |
|---|---|---|---|
| Re. 32,649 | 4/1988 | Brandt et al. | 604/368 |
| 4,093,765 | 6/1978 | Schmidt | 428/134 |
| 4,102,340 | 7/1978 | Mesek et al. | 128/287 |
| 4,519,799 | 5/1985 | Sakurai et al. | 604/366 |
| 4,590,114 | 5/1986 | Holtman | 428/171 |
| 4,610,678 | 9/1986 | Weisman et al. | 604/368 |
| 4,610,685 | 9/1986 | Raley | 604/366 |
| 4,636,209 | 1/1987 | Lassen | 604/378 |
| 4,655,757 | 4/1987 | McFarland et al. | 604/366 |
| 4,673,402 | 6/1987 | Weisman et al. | 604/368 |
| 4,699,619 | 10/1987 | Bernardin | 604/378 |
| 4,699,620 | 10/1987 | Bernardin | 604/385 A |
| 4,798,603 | 1/1989 | Meyer et al. | 604/378 |
| 4,822,453 | 4/1989 | Dean et al. | 162/157.6 |
| 4,859,527 | 8/1989 | DiStefano | 604/375 |
| 4,872,870 | 10/1989 | Jackson | 604/366 |
| 4,885,204 | 12/1989 | Bither et al. | 604/375 |
| 4,888,093 | 12/1989 | Dean et al. | 162/157.6 |
| 4,888,231 | 12/1989 | Angstadt | 428/213 |
| 4,889,595 | 12/1989 | Herron et al. | 162/157.6 |
| 4,889,596 | 12/1989 | Schoggen et al. | 162/157.6 |
| 4,889,597 | 12/1989 | Bourbon et al. | 162/157.6 |
| 4,898,642 | 2/1990 | Moore et al. | 162/157.6 |
| 4,911,700 | 3/1990 | Makoui et al. | 604/375 |
| 4,935,022 | 6/1990 | Lash et al. | 604/368 |

(List continued on next page.)

FOREIGN PATENT DOCUMENTS

| | | |
|---|---|---|
| 343940 | 11/1989 | European Pat. Off. . |
| 343941 | 11/1989 | European Pat. Off. . |
| 399564 | 11/1990 | European Pat. Off. . |
| 397110 | 11/1990 | European Pat. Off. . |
| 410480 | 1/1991 | European Pat. Off. . |
| 427317 | 5/1991 | European Pat. Off. . |
| 440472 | 8/1991 | European Pat. Off. . |
| 2078527 | 1/1982 | United Kingdom . |

OTHER PUBLICATIONS

P. G. Bither—"Thermally Bonded Cores Add Value to Absorbent Products" Nonwovens World, Jan., 1988, pp. 63–68.

P. G. Bither—"Thermally Bonded Absorbent Pads—The Next Generation?" Nonwovens World, Nov., 1986, pp. 49–55.

*Primary Examiner*—Robert A. H. Clarke
*Attorney, Agent, or Firm*—George W. Allen; Carl J. Roof; Eric W. Guttag

[57] ABSTRACT

Absorbent structures having a fluid acquisition/distribution layer with an average dry density of less than about 0.30 g/cc, an average density upon wetting with 1.0%, NaCl aqueous solution of less than about 0.20 g/cc, and an average dry basis weight from about 0.001 to about 0.10 g/cm$^2$; and a fluid storage layer positioned beneath the acquisition/distribution layer comprising at least about 15% superabsorbent material. The fluid acquisition/distribution layer comprises from about 50% to 100% chemically stiffened cellulosic fibers and from 0% to about 50% binding means.

25 Claims, 3 Drawing Sheets

U.S. PATENT DOCUMENTS

| | | | |
|---|---|---|---|
| 4,988,344 | 1/1991 | Reising et al. | |
| 4,988,345 | 1/1991 | Reising | 604/368 |
| 4,994,037 | 2/1991 | Bernardin | 604/368 |
| 5,009,650 | 4/1991 | Bernardin | 604/378 |
| 5,030,229 | 7/1991 | Yang | 604/370 |
| 5,217,445 | 6/1993 | Young et al. | 604/381 |
| 5,300,054 | 4/1994 | Feist et al. | |
| 5,304,161 | 4/1994 | Ahr et al. | |
| 5,350,370 | 9/1994 | Jackson et al. | 604/365 |
| 5,360,420 | 11/1994 | Cook et al. | 604/378 |
| 5,364,382 | 11/1995 | Latimer et al. | 604/378 |
| 5,391,161 | 2/1995 | Hellgren et al. | 604/366 |
| 5,429,629 | 7/1995 | Latimer et al. | 604/366 |

ABSORBENT STRUCTURES CONTAINING THERMALLY-BONDED STIFFENED FIBERS AND SUPERABSORBENT MATERIAL

This is a continuation of application Ser. No. 07/625,776, filed on Dec. 17, 1990, now U.S. Pat. No. 5,360,420 which is a continuation in part of application Ser. No. 07/468,549, filed Jan. 23, 1990, now abandoned.

FIELD OF THE INVENTION

This invention relates to absorbent structures using both cellulosic fiber material and superabsorbent material. The absorbent structures can be used in a variety of absorbent articles such as disposable diapers, adult incontinence pads and briefs and the like which are required to handle relatively large amounts of discharged body fluids, especially repeated discharges of relatively large amounts of fluid in relatively short amounts of time.

BACKGROUND OF THE INVENTION

Absorbent webs which comprise entangled masses of fibers, i.e., fibrous webs, are well known in the art. Such webs can imbibe liquids, such as discharged body fluids, both by an absorption mechanism wherein fluid is taken up by the fiber material itself and by a wicking mechanism wherein fluid is acquired by, distributed through and stored in the capillary interstices between fibers. One means for improving the absorbency characteristics of such fibrous web structures is to incorporate therein superabsorbent material, such as as polymeric gelling material (also referred to as hydrogel-forming material superabsorbent polymers, etc.) which imbibe fluid. The superabsorbent material serves to retain fluid such as discharged body liquids. An absorbent structure of this type wherein hydrogel-forming materials in particulate form are incorporated into fibrous webs is disclosed in Weisman and Goldman; U.S. Pat. No. 4,610,678; Issued Sep. 9, 1986.

The improvement in absorbency provided by incorporation of absorbent gelling materials has permitted the realization of absorbent articles such as diapers which employ relatively thin absorbent cores and which are, therefore, relatively thin products. Thinner diapers are less bulky to wear and fit better under clothing. They are also more compact in the package, making the diapers easier for the consumer to carry and store. Compactness in packaging also results in reduced distribution costs for the manufacturer and distributor.

One such absorbent core configuration which is useful for use as the absorbent structure in relatively thin absorbent articles is disclosed in U.S. Pat. No. 4,765,780, issued Aug. 23, 1988 (Angstadt). This patent discloses absorbent articles, such as diapers, which have a two layer absorbent core configuration wherein the core comprises an upper primary layer and a lower dusting layer. The primary layer is an airlaid web of hydrophilic fiber material with a substantial amount of absorbent gelling material admixed therewith. The dusting layer comprises hydrophilic fiber material and, preferably, contains no absorbent gelling material.

Another absorbent core configuration is disclosed in Weisman/Houghton/Gellert, U.S. Pat. No. 4,673,402, issued Jun. 16, 1987. This patent discloses absorbent articles having a dual layer absorbent core. In the dual layer configuration, the core comprises an upper primary layer which is an airlaid web of hydrophilic fiber material, optionally with a small amount of polymeric gelling agent particles admixed therewith. The core also comprises an underlying insert layer which is an airlaid mixture of hydrophilic fiber material and a substantial amount of polymeric gelling agent particles. This insert layer is generally positioned toward the front of the absorbent article such that more than half of the polymeric gelling agent material in the article is found in the front half thereof. Absorbent articles having the particular dual layer configuration of the '402 patent can be prepared in the form of especially thin, highly effective, low leakage diaper products.

Notwithstanding the existence of absorbent cores as described above, there remains a need to provide absorbent cores with improved effective absorbent capacity. One way to theoretically do this would be to increase the level of polymeric gelling material in the absorbent core. Unfortunately, high levels of polymeric gelling material, (especially levels in excess of about 15%) in fibrous webs typically used in absorbent cores tends to induce a phenomena referred to as gel-blocking. Gel-blocking occurs when the polymeric gelling material located in regions first contacted with fluid increase in volume as a consequence of imbibing the fluid and forming the hydrogel. When polymeric gelling material concentration is too high, the hydrogel can block additional fluid from reaching other regions of the core having unused absorbent capacity. The occurrence of gel blocking can lead to leakage during usage of the absorbent article.

Polymeric gelling materials have been developed which can exhibit a reduced tendency to result in gel blocking. Such materials are described in RE U.S. Pat. No. 32,649, Apr. 19, 1988, Brandt/Goldman/Inglin. However, these improved polymeric gelling materials, and other superabsorbent materials, are subject to performance limitations of the web of cellulosic fibers in which particles of gelling material are distributed. In particular, upon initial wetting, the cellulosic fibers become highly flexible and the web tends to collapse to a higher density and, consequently, exhibits smaller average pore size. Whereas, pore size becomes smaller than the pore size in regions of the web not yet wetted, a capillary gradient is created which opposes efficient transport of fluids to the dry areas of the absorbent article.

Another reason why many absorbent articles such as diapers are subject to leakage is inability to absorb second and subsequent discharges of fluid even if the first fluid discharge has been effectively absorbed. Leakage due to second and subsequent discharges is especially prevalent during the night, when users commonly experience multiple discharges before being attended to. One reason for the inability of many absorbent articles to adequately handle multiple discharges of fluid, in addition to the reasons discussed above, is the inability of the absorbent core to transport discharged fluid away from the region of discharge once the absorbent capacity of that region has been reached. After a discharge of fluid occurs, the fluid tends to remain situated in the region proximate to the discharge. The occurrence of successive voiding of fluid creates a driving force to laterally transport the previous fluid and newly discharged fluid. However, actual performance of the absorbent article is limited by the ability to have the fluid transported to the farther reaches of the core. In this regard, even in the absence of polymeric gelling material, the overall absorbent capacity of conventional absorbent diaper cores is generally incompletely utilized prior to failure, i.e., leakage, of the absorbent article.

Yet another reason for leakage in conventional absorbent articles is the propensity of the cellulosic fibers conventionally utilized for fluid acquisition and distribution to collapse upon wetting, thus impairing permeability of the structures.

It is an object of this invention to provide superabsorbent-containing absorbent structures which can circumvent the problems of gel blocking and wet collapse and which can utilize an increased proportion of their absorbent capacity.

It is a further object of this invention to provide superabsorbent-containing absorbent structures which can acquire fluid rapidly in the region of discharge and transport the fluid over relatively large proportion of the absorbent structure storage area and, additionally, be capable of effectively acquiring and distributing discharged bodily fluid from second or other successive voiding.

It is yet another object of this invention to provide absorbent structures which are capable of meeting the objects described above which are of a relatively thin design.

One absorbent structure which has been suggested is described in U.S. Pat. No. 4,935,022, issued Jun. 19, 1990 to Glen R. Lash and Leonard R. Thompson. This patent discloses disposable absorbent articles comprising a layered absorbent core positioned between a backsheet and a topsheet, wherein the absorbent core comprises an upper layer of stiffened, twisted, curled cellulose fibers and requires from about 3% to 15%, by weight, of large particle absorbent gelling material and a lower layer of stiffened, twisted, curled cellulose fibers and from about 15% to 60%, by weight, of absorbent gelling material. The upper layer serves the principal purpose of acquisition and distribution of bodily fluid discharges. The stiffened, twisted, curled fibers are highly beneficial in this regard. The lower layer, which is necessarily smaller than the upper layer, is principally for fluid storage.

Another absorbent structure which has been proposed is described in U.S. Pat. No. 4,798,603, S. C. Meyer et al., issued Jan. 17, 1989, titled "Absorbent Article Having a Hydrophobic Transport Layer." As suggested by the title, this patent describes an absorbent article with a hydrophobic transport layer, made from known hydrophobic synthetic fibers. The transport layer is positioned between a topsheet and an absorbent body. The absorbent body is necessarily more hydrophilic than the transport layer. The purpose of the transport layer is to act as an insulating layer between the topsheet and the absorbent body, to reduce skin wetness. Regardless of whether the structures described therein meet this objective, the hydrophobic nature of the transport layer of U.S. Pat. No. 4,798,603 would be expected to have limited fluid acquisition and fluid transport properties due, at least in part, to the hydrophobicity of the layer. This would be particularly so for second and successive fluid discharges after which any optional surfactants have been washed away.

Notwithstanding the existence of absorbent articles of the type described above, there is a need to identify further improved configurations for absorbent articles which provide improved fluid distribution and acquisition performance, especially with respect to successive fluid discharges.

Accordingly, the present invention provides improved absorbent structures, and elements for use therein, as well as absorbent articles utilizing such structures, utilizing a multiple layer absorbent core that effectively and efficiently acquires the wearer's discharged body fluids upon initial and successive discharges, transports acquired fluid, from both initial and successive discharges over a relatively large proportion of the absorbent structure surface area, and stores such discharged fluids.

SUMMARY OF THE INVENTION

The present invention provides an absorbent structure, which is particularly useful as the absorbent core in disposable absorbent articles such as diapers and incontinence briefs, and which comprises: a) a fluid acquisition/distribution layer having an average dry density of less than about 0.30 g/cc, an average density upon wetting to saturation with 1% NaCl aqueous solution, on a dry weight basis, of less than about 0.20 g/cc, and an average dry basis weight of from about 0.001 to about 0.10 g/cm$^2$; and a fluid storage layer, positioned beneath the acquisition/distribution layer. The acquisition/distribution layer comprises a web of from about 50% to 100%, by weight, chemically stiffened cellulosic fibers and from 0% to about 50%, by weight, of a binding means. The binding means can be used to increase physical integrity of the web to facilitate processing and/or improve in-use performance, and/or increase effective average inter-fiber pore size of the web. As used herein, binding means refers to means incorporated integral to the layer of stiffened fibers, such as (but not limited to) nonstiffened cellulosic materials, synthetic fibers, chemical additives, and thermoplastic polymers. Tissue envelopes and other scrim external to the acquisition/distribution layer can also be used to enhance physical integrity in combination with, or in place of, said binding means.

The storage layer comprises at least about 15%, by weight, of superabsorbent material and from 0% to about 85% of a carrier means for the superabsorbent material. The fluid acquisition/distribution layer should contain no more than about 6.0% of superabsorbent material. Preferably, the acquisition/distribution layer will be substantially free of superabsorbent material. For purposes herein, "substantially free" of superabsorbent material means less than about 2.0%, preferably less than about 1.0%, more preferably zero or essentially zero percent superabsorbent material. As used herein, "essentially zero" percent superabsorbent material means low amounts (less than about 0.5%) of superabsorbent material present in the acquisition/distribution layer incidental to the contact or close proximity of the superabsorbent-containing storage layer with the acquisition/distribution layer.

The fluid acquisition/distribution layer has a top surface area which is at least 15% of the top surface area of the fluid storage layer, but which is smaller than the top surface area of the fluid storage layer. The acquisition/distribution layer is preferably positioned relative to the fluid storage such that in the unfolded planar configuration of the article none of its surface area extends beyond the boundaries of the top surface area of the fluid storage layer. More preferably the acquisition/distribution layer has a top surface area which is from about 15% to about 95%, most preferably from about 25% to about 90%, of the top surface area of the fluid storage layer.

The absorbent structure can be advantageously utilized as the absorbent core in absorbent articles, e.g., disposable diapers and incontinence briefs, which also comprise a fluid pervious topsheet and a fluid impervious backsheet affixed to the topsheet, wherein the absorbent core is disposed therebetween. The absorbent core is positioned such that the acquisition/distribution layer is located between the topsheet and the storage layer, and the storage layer is located between the acquisition/distribution layer and the backsheet.

The superabsorbent material used in the storage layer has an Absorbent Capacity of at least about 10 grams of Synthetic Urine (1.0% NaCl aqueous (distilled water) solution) per gram of superabsorbent material, measured according to the test procedure hereinafter described. Suitable superabsorbent material categories include polymeric absorbent gelling materials, typically utilized in the form of discrete particles, and superabsorbent fibers, such as acrylate grafted fibers and superabsorbent modified cellulosic fibers.

DETAILED DESCRIPTION OF THE INVENTION

Figure 1:
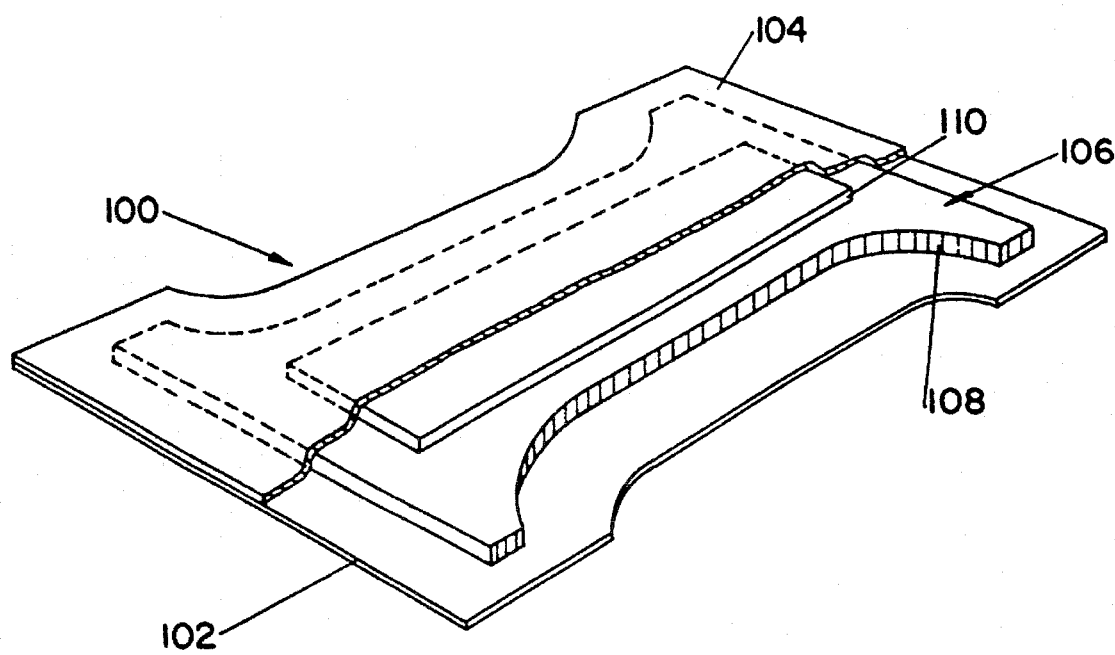
FIG. 1 represents a perspective view of a diaper with an absorbent core having the multiple layer configuration of the present invention. The absorbent core shown has a rectangular-shaped acquisition/distribution layer and an hour glass-shaped storage layer.

The absorbent structures of the present invention can be utilized in disposable products which are capable of absorbing significant quantities of body fluids, such as urine and water in body wastes. Such articles may be prepared in the form of disposable diapers, adult incontinence briefs, adult incontinence pads and the like.

The absorbent articles herein generally comprise three basic structural components. One such component is a liquid impervious backsheet. On top of this backsheet is disposed an absorbent core which itself comprises two distinct layers, and which includes a superabsorbent material in one of the layers. On top of this absorbent core and Joined to the backsheet is a water pervious topsheet. The topsheet is the element of the article which is placed next to the skin of the wearer. As used herein, the term "joined" encompasses configurations whereby the topsheet is directly joined to the backsheet by affixing the topsheet directly to the backsheet, and configurations whereby the topsheet is indirectly joined to the backsheet by affixing the topsheet to intermediate members which in turn are affixed to the backsheet. Preferably, the topsheet and backsheet are Joined directly at the diaper periphery by adhesive or other attachment means known in the art.

Especially preferred absorbent articles of this invention are disposable diapers. Articles in the form of disposable diapers are fully described in Duncan and Baker, Re U.S. Pat. No. 26,151, Issued Jan. 31, 1967; Duncan, U.S. Pat. No. 3,592,194, Issued Jul. 13, 1971; Duncan and Gellert, U.S. Pat. No. 3,489,148, Issued Jan. 13, 1970; and Buell, U.S. Pat. No. 3,860,003, Issued Jan. 14, 1975; which patents are incorporated herein by reference. A preferred disposable diaper for the purpose of this invention comprises an absorbent core; a topsheet superposed or co-extensive with one face of the core, and a liquid impervious backsheet superposed or co-extensive with the face of the core opposite the face covered by the topsheet. Both the backsheet and the topsheet most preferably have a width greater than that of the core thereby providing side marginal portions of the backsheet and topsheet which extend beyond the core. Frequently the backsheet and the topsheet will be fused together in these side marginal portions. The diaper is preferably constructed in a shaped configuration such as, but not limited to, an hourglass shape.

The backsheet of the articles herein can be constructed, for example, from a thin, plastic film of polyethylene, polypropylene, or other flexible moisture impeding material which is substantially water impervious. Polyethylene, having an embossed caliper of approximately 1.5 mils, is especially preferred.

The topsheet of the article herein can be made in part or completely of synthetic fibers or films comprising such materials as polyester, polyolefin, rayon, or the like, or of natural fibers such as cotton. In nonwoven topsheets, the fibers are typically bound together by a thermal binding procedure or by a polymeric binder such as polyacrylate. This sheet is substantially porous and permits a fluid to readily pass therethrough into the underlying absorbent core.

Another suitable type of topsheet comprises the topsheets formed from liquid impervious polymeric material such as polyolefins. Such topsheets can have tapered capillaries of certain diameter and taper positioned in the topsheet to permit flow of discharged fluid through the topsheet into the underlying absorbent core of the article.

The topsheets used in the articles of the present invention should be relatively hydrophobic in comparison with the absorbent core of said articles. Topsheet construction is generally disclosed in Davidson, U.S. Pat. No. 2,905,176, Issued Sep. 22, 1959; Del Guercio, U.S. Pat. No. 3,063,452, issued Nov. 13, 1962; Holliday, U.S. Pat. No. 3,113,570, Issued Dec. 10, 1963, and Thompson, U.S. Pat. No. 3,929,135; Issued Dec. 30, 1975; which patents are incorporated herein by reference. Preferred topsheets are constructed from polyester, rayon, rayon/polyester blends, polyethylene or polypropylene. The topsheet can be treated with surfactant to make it more wettable and therefore relatively less hydrophobic, to thereby increase fluid flow through it at least upon initial wetting. However, the topsheet should still be more hydrophobic than the absorbent article element which receives fluids after passing through the topsheet.

An absorbent core, which is preferably flexible, is positioned between the elongated backsheet and the topsheet to form the absorbent articles herein. This core essentially comprises both an upper fluid acquisition/distribution layer and a lower fluid storage layer. It should be understood that for purposes of this invention these two types of layers refer merely to the upper and lower zones of the absorbent core and are not necessarily limited to single layers or sheets of material. Thus both the fluid acquisition/distribution layer and the fluid storage layer may actually comprise laminates or combinations of several sheets or webs of the requisite type of materials as hereinafter described. The storage layer can comprise a single sheet of essentially 100% superabsorbent material, as will be hereinafter described. As used herein, the term "layer" includes the terms "layers" and "layered." For purposes of this invention, it should also be understood that the term "upper" refers to the layer of the absorbent core which is nearest to and faces the article topsheet; conversely, the term "lower" refers to the layer of the absorbent core which is nearest to and faces the article backsheet.

Optionally, a fluid pervious sheet (e.g., a tissue sheet) or other scrim is positioned between the acquisition/distribution layer and the storage layer to increase integrity of the acquisition/distribution layer during processing and/or use. Such sheet or scrim can envelope all or part of acquisition/distribution layer, or simply be positioned as described above without necessarily enveloping the acquisition/distribution layer. Also, optionally, the superabsorbent material-containing storage layer can be enveloped with a fluid pervious sheet, such as a tissue paper sheet, to obviate user concerns with loose superabsorbent material.

Acquisition/Distribution Layer

One essential element of the absorbent structures hereof is an upper fluid acquisition/distribution layer which comprises a combination of a hydrophilic fibrous material, described more fully hereinafter. This fluid acquisition/ distribution layer serves to quickly collect and temporarily hold discharged body fluid. A portion of discharged fluid may, depending upon the wearer's position, permeate the acquisition/distribution layer and be absorbed by the storage layer in the area proximate to the discharge. However, since fluid is typically discharged in gushes, the storage layer in such area may not absorb the fluid as quickly as it is discharged. Therefore, the upper acquisition/distribution layer hereof also facilitates transport of the fluid from the point of initial fluid contact to other parts of the acquisition/ distribution layer. In the context of the present invention, it should be noted that the term "fluid" means "liquid."

As previously noted, the fluid acquisition/distribution layer is a web comprising stiffened cellulosic fibers. The acquisition layer comprises from about 50% to 100% of these fibers and from 0% to about 50% of a binding means. Suitable binding means are discussed below.

The fluid distribution function of the acquisition/distribution layer is of particular importance in order to more fully utilize the capacity of the storage section. The presence of substantial amounts of superabsorbent materials in the acquisition/distribution layer which swell upon contact with fluids is believed to adversely affect this function of the acquisition/distribution layer.

A variety of other factors relating to the fluid acquisition/ distribution layer of the absorbent structures herein can be of importance in determining the effectiveness of the resulting absorbent articles. These include shape, basis weight, density, permeability, capillarity and wicking ability, the type and structural integrity, and character of the fibrous material utilized. As indicated, the acquisition/distribution layer of the core is preferably elongated. For purposes of this invention, this means that the acquisition/distribution layer, like the storage layer, is elongated if it is of unequal length and width in the unfolded, flat configuration. The acquisition/ distribution layer in the unfolded configuration can be of any desired shape, for example, rectangular, trapezoidal, oval, oblong or hourglass-shaped. The shape of the upper fluid acquisition/distribution layer of the core can, but need not necessarily, correspond to the general shape of the storage layer. The top surface area of the acquisition/distribution layer will preferably range from about 25% to about 90% of the top surface area of the storage layer, and also preferably will not extend beyond the edge of the storage layer at any outer boundary. The acquisition/distribution layer will typically have top surface area less than about 80% of that of thin storage layer.

Preferably, there is a margin from the edge of the acquisition/distribution layer to the edge of the storage layer of at least about 0.5 cm, preferably at least about 1.25 cm, in the regions proximate to where fluid is discharged during use. In diapers, this would correspond, for example, to the crotch region 115 of FIG. 2, particularly at the narrowest part of the storage core 106 in the central region 115. Additionally, especially for absorbent articles to be worn by males, such a margin is maintained in the front waist region, exemplified as 112 in FIG. 2, which area is to be worn on the front of the wearer.

The fluid acquisition/distribution layer will generally have an average dry density of less than about 0.30 g/cm$^3$, measured prior to use, and an average density upon wetting to saturation with Synthetic Urine (1.0% NaCl aqueous solution, with distilled water), on a dry weight basis, of less than about 0.20 g/cm$^3$, preferably less than about 0.15 g/cm$^3$. Also, preferably, the average dry density and density upon wetting to saturation are between about 0.02 g/cm$^3$ and 0.20 g/cm$^3$, more preferably between about 0.02 g/cm$^3$ and about 0.15 g/cm$^3$. The average dry basis weight of the acquisition/distribution layer of the absorbent core will typically range from about 0.001 to about 0.10 g/cm$^2$, preferably from about 0.01 to about 0.08 g/cm$^2$, more preferably from about 0.015 to about 0.04 g/cm$^2$. Unless specifically indicated, all basis weights and density values are calculated on a dry basis (at equilibrium moisture levels no greater than about 6%). Density and basis weight can be substantially uniform although nonuniform density and/or basis weight, and density and/or basis weight gradients, are meant to be encompassed herein. Thus, the acquisition/ distribution layer can contain regions of relatively higher or relatively lower density and basis weight, preferably not exceeding the foregoing ranges. Average dry density and average dry density upon wetting to saturation with Synthetic Urine (1.0% NaCl aqueous solution, with distilled water) values are calculated from basis weight of the dry layer and layer caliper. Dry caliper and caliper upon wetting to saturation are measured under a confining pressure of 0.2 psi (1.43 kPa). Average density upon wetting to saturation is calculated from the dry basis weight and saturation caliper. The saturation caliper is measured after the layer is saturated (under unrestrained conditions) with the 1.0% NaCl aqueous solution and allowed to equilibrate.

The acquisition/distribution layer of the absorbent structures herein essentially comprises a web of hydrophilic chemically stiffened cellulosic fibers. These cellulosic fibers are typically wood pulp fibers which have been stiffened with an intrafiber chemical stiffening agent.

The fluid acquisition/distribution layer should contain no more than about 6.0% of superabsorbent material. Preferably, the acquisition/distribution layer will be substantially free of superabsorbent material. For purposes herein, "substantially free" of superabsorbent material means less than about 2.0%, preferably less than about 1.0%, more preferably zero or essentially zero percent superabsorbent material. As used herein, "essentially zero" percent superabsorbent material means low amounts (less than about 0.5%) of superabsorbent material present in the acquisition/distribution layer incidental to the contact or close proximity of the superabsorbent-containing storage layer with the acquisition/distribution layer.

If present in the acquisition/distribution layer, especially if present in amounts greater than about 2.0%, superabsorbent material in the form of particles of absorbent gelling material may be of relatively large diameter (e.g., from about 400 to about 700 microns in mass median particle size). Superabsorbent particles having a mass median particle size less than 400 microns may also be employed.

As discussed above, the articles of the present invention employ chemically stiffened fibers. As used herein, the term "chemically stiffened fibers" means any fibers which have been stiffened by chemical means to increase stiffness of the fibers under both dry and aqueous conditions. Such means include the addition of chemical stiffening agents which, for example, coat and/or impregnate the fibers. Such means also include the stiffening of the fibers by altering the chemical structure of the fibers themselves, e.g., by cross-linking polymer chains.

For exemplary purposes, polymeric stiffening agents which can coat or impregnate cellulosic fibers include: cationic modified starch having nitrogen-containing groups (e.g., amino groups) such as those available from National Starch and Chemical Corp., Bridgewater, N.J., USA; latex; wet strength resins such as polyamide-epichlorohydrin resin (e.g., Kymene™ 557H, Hercules, Inc. Wilmington, Del., USA), polyacrylamide resin (described, for example, in U.S.

Pat. No. 3,556,932 issued Jan. 19, 1971 to Coscia, et al.; also, for example, the commercially available polyacrylamide marketed by American Cyanamid Co., Stanford, Conn., USA, under the tradename Parez™ 631 NC); urea formaldehyde and melamine formaldehyde resins, and polyethylenimine resins. A general dissertation on wet strength resins utilized in the paper art, and generally applicable herein, can be found in TAPPI monograph series No. 29. "Wet Strength in Paper and Paperboard", Technical Association of the Pulp and Paper Industry (New York, 1965).

The fibers utilized in the structures herein can also be stiffened by means of chemical reaction. For example, crosslinking agents can be applied to the fibers which, subsequent to application, are caused to chemically form intra-fiber crosslink bonds. These crosslink bonds can increase stiffness of the fibers. Whereas the utilization of intrafiber crosslink bonds to chemically stiffen the fiber's is preferred, it is not meant to exclude other types of reactions for chemical stiffening of the fibers.

Fibers stiffened by crosslink bonds in individualized (i.e., fluffed) form are disclosed, for example, in Bernardin, U.S. Pat. No. 3,224,926, Issued Dec. 21, 1965; Chung, U.S. Pat. No. 3,440,135, Issued Apr. 22, 1969;. Chatterjee, U.S. Pat. No. 3,932,209, Issued Jan. 13, 1976 and Sangenis et al., U.S. Pat. No. 4,035,147, Issued Jul. 12, 1977. More preferred fibers are disclosed in Dean et al., U.S. Pat. No. 4,822,453, issued Apr. 18, 1989, Dean et al., U.S. Pat. No. 4,888,093, issued Dec. 19, 1989, and Moore et al., U.S. Pat. No. 4,898,642, issued Feb. 6, 1990. All of these patents are incorporated herein by reference. In addition to being hydrophilic, these stiffened fibers remain stiff even upon wetting; thus webs made from them do not collapse, as do webs made from conventional unstiffened fibers when wet. This provides improved ability to acquire and distribute fluids in second and subsequent discharges.

In the more preferred stiffened fibers, chemical processing includes intrafiber crosslinking with crosslinking agents while such fibers are in a relatively dehydrated, defibrated (i.e, individualized), twisted, curled condition. Suitable chemical stiffening agents include monomeric crosslinking agents including, but not limited to, $C_2$–$C_8$ dialdehydes and $C_2$–$C_8$ monoaldehydes having an acid functionality can be employed to form the crosslinking solution. These compounds are capable of reacting with at least two hydroxyl groups in it single cellulose chain or on proximately located cellulose chains in a single fiber. Such crosslinking agents contemplated for use in preparing the stiffened cellulose fibers include, but are not limited to, glutaraldehyde, glyoxal, formaldehyde, and glyoxylic acid. Other suitable stiffening agents are polycarboxylates, such as citric acid. The polycarboxylic stiffening agents and a process for making stiffened fibers from them are described in U.S. Ser. No. 596,606, filed Oct. 17, 1990, incorporated by reference herein. The effect of crosslinking under these conditions is to form fibers which are stiffened and which tend to retain their twisted, curled configuration during use in the absorbent articles herein. Such fibers, and processes for making them are described in the above incorporated patents.

The preferred stiffened fibers are twisted and curled can be quantified by referencing both a fiber "twist count" and a fiber "curl factor". As used herein, the term "twist count" refers to the number of twist nodes present in a certain length of fiber. Twist count is utilized as a means of measuring the degree to which a fiber is rotated about its longitudinal axis. The term "twist node" refers to a substantially axial rotation of 180° about the longitudinal axis of the fiber, wherein a portion of the fiber (i.e., the "node") appears dark relative to the rest of the fiber when viewed under a microscope with transmitted light. The twist node appears dark at locations wherein the transmitted light passes through an additional fiber wall due to the aforementioned rotation. The distance between nodes corresponds to an axial rotation of 180°. The number of twist nodes in a certain length of fibers (i.e., the twist count) is directly indicative of the degree of fiber twist, which is a physical parameter of the fiber. The procedures for determining twist nodes and total twist count are described in the hereinbefore referenced U.S. Pat. No. 4,898,642.

The preferred stiffened cellulose fibers will have an average dry fiber twist count of at least about 2.7, preferably at least about 4.5 twist, nodes per millimeter. Furthermore, the average wet fiber twist count of these fibers should preferably be at least about 1.8, preferably at least about 3.0, and should also preferably be at least about 0.5 twist nodes per millimeter less than the average dry fiber twist count. Even more preferably, the average dry fiber twist count should be at least about 5.5 twist nodes per millimeter, and the average wet fiber twist count should be at least about 4.0 twist nodes per millimeter and should also be at least 1.0 twist nodes per millimeter less than its average dry fiber twist count. Most preferably, the average dry fiber twist count should be at least about 6.5 twist nodes per millimeter, and the average wet fiber twist count should be at least about 5.0 twist nodes per millimeter and should also be at least 1.0 twist nodes per millimeter less than the average dry fiber twist count.

In addition to being twisted, the preferred fibers used in the acquisition/distribution layer of the absorbent structure are also curled. Fiber curl may be described as the fractional shortening of the fiber due to kinks, twists, and/or bends in the fiber. For the purposes of this invention, fiber curl is measured in terms of a two dimensional plane. The extent of fiber curling can be quantified by referencing a fiber curl factor. The fiber curl factor, a two dimensional measurement of curl, is determined by viewing the fiber in a two dimensional plane. To determine curl factor, the projected length of the fiber as the longest dimension of a two dimensional rectangle encompassing the fiber, $L_R$, and the actual length of the fiber, $L_A$, are both measured. The fiber curl factor can then be calculated from the following equation:

$$Curl\ Factor = (L_A/L_R) - 1.$$

An image analysis method that can be utilized to measure $L_R$ and $L_A$ is described in U.S. Pat. No. 4,898,642. Preferably the fibers utilized in the layers of the absorbent core herein will have a curl factor of at least about 0.30, and more preferably will have a curl factor of at least about 0.50.

The degree of stiffening, dependent upon the type and amount of stiffening agent (i.e., crosslinking agent) used, the degree of dehydration of the fibers during curing of the crosslinking agent, and the curing time and conditions, affect the ability of the fiber to take up fluid and the tendency of the fiber to swell.

The fiber stiffness as it relates to resistance to fiber wall swelling can be quantified by referencing the water retention value (WRV) of the stiffened cellulosic fibers used in the absorbent articles herein. WRV is a measure of the amount of water retained by a mass of fibers after substantially all of the interfiber water has been removed. Another parameter which can be used to characterize the nature of the stiffened fibers formed by crosslinking fibers in relatively dehydrated form is that of alcohol retention value (ARV), ARV is a measure of the extent to which a fluid, e.g., isopropyl alcohol, which does not induce substantial fiber swelling, is taken up by the stiffened fibers. The ARV of the stiffened fibers is directly related to the extent that the fibers were swollen with the solution of crosslinking agent during the stiffening procedure. Relatively higher ARVs mean that the fibers were generally swollen to a relatively greater extent during crosslinking. Procedures for determining WRV and ARV are described in U.S. Pat. No. 4,898,642.

The WRV for the stiffened, twisted, curled fibers used in the present invention will preferably range between about 28% and about 50%. In more preferred embodiments, the WRV of the fibers can range from about 30% to 45%. Fibers having a WRV within these ranges are believed to provide an optimal balance of swelling-induced untwisting and fiber stiffness.

The stiffened cellulose fibers preferred for use herein are those which have an ARV (isopropol alcohol) of less than about 30%. The limitation that such fibers have an ARV (isopropol alcohol) of less than about 30% is indicative of the relatively dehydrated, unswollen state of these fibers during the stiffening process. More preferably, the ARV (isopropol alcohol) of the fibers useful herein will be less than about 27%.

The stiffened cellulose fibers herein having the preferred twist count, curl factor, WRV and ARV characteristics hereinbefore set forth, can be prepared by internally crosslinking such fibers in relatively dehydrated form while or after such fibers are being or have been dried and defibrated (i.e., "fluffed") as described in U.S. Pat. No. 4,898,642. It is not, however, meant to necessarily exclude other hydrophilic, chemically stiffened fibers from this invention, such other fibers being described in (but not limited to) the previously incorporated U.S. Pat. Nos. 3,224,926, 3,440,135, 4,035,147, and 3,932,209.

A characteristic of stiffened fibers, particularly the twisted, curled stiffened fibers is their ability to partially untwist and uncurl upon wetting. Thus, when formed into webs of sufficient density, the webs can expand upon wetting to an equilibrium wet density, which, when calculated, on a dry fiber density, is less than the average dry density (prior to wetting). This accounts for the average dry densities of up to about 0.30 g/cm$^3$ described above, in conjunction with lower average densities upon wetting to saturation. Such webs which can expand upon wetting are described in U.S. Pat. No. 4,822,453. To the extent that it is desired to utilize this characteristic in absorbent article design, those of ordinary skill in the art will be able to adjust the relative amount of stiffening agent used, and the extent to which twist and curl in the stiffened fibers is imparted, to achieve the desired amount of expansion upon wetting.

The stiffened cellulosic fibers can be provided in web form by various techniques, including airlaying and wetlaying.

Airlaid Webs

The stiffened cellulosic fibers can be airlaid to form the web of a desired density and basis weight. The stiffened fibers for use in the present invention can be airlaid according to techniques well known to those skilled in the art of airlaying cellulosic fibers. In general, airlaying can be effected by metering an air flow containing the fibers, in substantially dry condition, onto a wire screen and, optionally, compressing the resulting web to the desired density. Alternately, the fibers can be airlaid to the desired density without compression. The airlaid web will comprise at least about 50% of stiffened cellulosic fibers, as described above, and can comprise up to and including 100% of said fibers. The web can optionally contain binding means, such as described below, or other optional components, such as or ingredients modifying fluid handling properties (e.g., hydrophilic surface active agents), and the like.

Wetlaid Webs

In another embodiment, the stiffened cellulosic fibers, rather than being airlaid to form the web, are wetlaid. The wetlaid webs comprise from about 50% to 100% of the stiffened fibers and from 0% to about 50% of a blinding means for increasing physical integrity of the web, to facilitate processing in the wet and/or dry state, and to provide increased integrity upon wetting of the web during use. Preferably, the wetlaid webs will comprise at least about 2% of a fibrous binding means or high surface area cellulose binding means (hereafter described). Chemical additives can also be used as binding means, and are incorporated into the acquisition/distribution layer at levels typically of about 0.2% to about 2.0%, dry web weight basis.

Techniques for wetlaying cellulosic fibrous material to form sheets such as dry lap and paper are well known in the art. These techniques are generally applicable to the wetlaying of the stiffened fibers to form wetlaid sheets useful in the absorbent structures of this invention. Suitable wetlaying techniques include handsheeting, and wetlaying with the utilization of papermaking machines as disclosed, for instance, by L. H. Sanford et al. in U.S. Pat. No. 3,301,746. Due to the behavior of stiffened fibers, particularly their tendency to flocculate in aqueous slurries, certain processing modifications, hereafter described, are preferably implemented when wetlaying with papermaking machines. In general, wetlaid webs can be made by depositing an aqueous slurry of fibers on to a foraminous forming wire, dewatering the wetlaid slurry to form a wet web, and drying the wet web. Preferably, the aqueous slurries of fibers for wetlaying will have a fiber consistency of between about 0.05% and about 2.0%, preferably between about 0.05% and about 0.2%, total slurry weight basis. Deposition of the slurry is typically accomplished using an apparatus known in the art as a headbox. The headbox has an opening, known as a slice, for delivering the aqueous slurry of fibers onto the foraminous forming wire. The foraminous forming wire is often referred to in the art as a Fourdrinier wire. The Fourdrinier wire can be of construction and mesh size used for dry lap or other papermaking processing. Preferably, mesh sizes of about 70 to about 100 (Tyler standard screen scale) are used. (All mesh sizes referred to herein shall be based upon the Tyler standard screen scale, unless otherwise specifically indicated.) Conventional designs of headboxes known in the art for drylap and tissue sheet formation may be used. Suitable commercially available headboxes include, for example, fixed roof, twin wire, and drum former headboxes. Once formed, the wet web is dewatered and dried. Dewatering can be perforated with suction boxes or other vacuum devices. Typically, dewatering increases the fiber consistency to between about 8% and about 45%, total wet web weight basis, preferably between about 8% and about 22%. Dewatering to consistencies above about 22% may require wet-pressing and is less preferred. After dewatering, the web can be, but is not necessarily, transferred from the forming wire to a drying fabric which transports the web to drying apparatuses. The drying fabric is preferably coarser than the forming wire, for increased drying efficiency. The drying fabric preferably has about 30% to about 50% open area and about 15% to about 25% knuckle area, such as a 31×25 3S (satin weave) fabric that has been sanded to increase the knuckle area to within the preferred range. Wet microcontraction is preferably implemented during transfer from the forming wire to the fabric. Wet microcontraction can be accomplished by running the forming wire at a speed which is from about 5% to about 20% faster than the speed at which the fabric is being run. Drying can be accomplished with a thermal blow-through dryer or vacuum device such as a suction box, although thermal blow-through drying is preferred. The wetlaid webs are preferably dried to completion (generally to fiber consistency between about 90% and about 95%) by the thermal blow-through dryers. Blow-through drying is believed to efficiently dry webs of the stiffened fibers due to the high void volume of the webs. Steam drum drying apparatus known in the art, such as Yankee drum dryers, can be used but are less preferred. Drum dryers are believed to be less efficient for drying webs of the stiffened fibers and can also compact the webs. The dried webs are preferably not creped.

As an alternative to drying as described above, the dewatered web can be removed from the forming wire placed on a drying screen and dried (unrestrained) in a batch, drying process by, for example, a thermal blow through dryer or a forced convection steam heated oven.

The stiffened fibers have the tendency to flocculate, or form clumps, in aqueous solution. In order to inhibit flocculation, the aqueous slurry should be pumped to the headbox at a linear velocity of at least about 0.25 m/sec. Also, it is preferred that the linear velocity of the slurry upon exit from the headbox slice is from about 2.0 to about 4.0 times the velocity of the forming wire. Another method for reducing flocculations of fibers in a wetlaying process is described in U.S. Pat. No. 4,889,597, issued Dec. 26, 1989, incorporated herein by reference, wherein jets of water are directed at the wetlaid fibers just after deposition on the forming wire.

Binding Means

Relative to conventional non-stiffened cellulosic fibers, the crosslinked, twisted, stiffened fibers as described above form lower tensile strength sheets, particular in the undried condition. Therefore, in order to facilitate processing and to increase the integrity of the webs, particularly for wetlaid webs (although binding means can also be used with airlaid webs), a binding means can be integrally incorporated into or onto the web. This can be done by adding the binding means to the fibers prior to web formation (wetlaid or airlaid web, formations), by applying the binding means (e.g., chemical additive binding means) to a wetlaid web after deposition on the forming wire and before drying, by applying binding means to a dry web (wetlaid), or a combination thereof.

Suitable binding means for addition to the stiffened cellulosic fibers prior to formation of the wet web from a pulp slurry include, but are not limited to, a variety of cellulosic and synthetic fibrous materials. Such material include non-stiffened cellulosic fibers (i.e., conventional cellulosic pulp fibers), highly refined, nonstiffened, cellulosic fibers which are refined to Canadian Standard Freeness (CSF) of less than about 200 CSF, more preferably from about 100 CSF to about 200 CSF (highly refined fibers being referred to herein as "crill", and high surface area cellulosic material such as expanded cellulose fibers (hereinafter described).

Various types of synthetic fibrous material can be used in the synthetic fiber binding means. For the purposes hereof, the use of "synthetic fibrous materials" as a binding means shall refer to the utilization of such fibrous materials, in the final product, in fibrous form. (Preferably, the synthetic fibers are of at least staple length, i.e., the fibers preferably having an average length of at least about 1.5 cm). Any type of fibrous material which is suitable for use in conventional absorbent products is believed to be suitable for use in the acquisition/distribution web of the present invention. Specific examples of such fibrous material include modified cellulose fibers, rayon, polyester fibers such as polyethylene terephthalate (DACRON), hydrophilic nylon (HYDROFIL) and the like. Other fibers useful include cellulose acetate, polyvinyl fluoride, polyvinylidene chloride, acrylics, polyvinyl acetate, polyamides (such as nylon), bicomponent fibers, tricomponent fibers, mixtures thereof, and the like. Hydrophilic fibrous materials are preferred. Examples of suitable hydrophilic fibrous materials include hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. Hydrophobic synthetic fibers can also be used, but are less preferred. Such synthetic fibers that can be added to the web and utilized in the final web product in fibrous form include rayon, polyethylene, polypropylene, etc. Such fibers, when of a hydrophobic nature, are preferably present in quantities of less than about 30%, total web weight basis, such that the web remains substantially hydrophilic. Conventionally, non-stiffened fibers, crill, and synthetic fibers can also be used in airlaid webs.

In one preferred embodiment wherein the acquisition/distribution layer is made by a wetlaying process, the web comprises from about 85% to about 95% of the stiffened cellulosic fibers and from about 5% to about 15% of crill, preferably from about 90% to about 95% of the stiffened fibers and from about 5% to about 10% of crill, most preferably about 92% of stiffened fibers and about 8% crill. Suitable cellulosic fibers for use as crill include chemically pulped wood fibers, including softwood and hardwood pulp fibers, preferably southern softwood fibers (e.g., Foley Fluff, The Procter & Gamble Cellulose Co., Memphis, Tenn., USA). All percentages of web components referred to herein, unless otherwise expressly stated, are on a dry web total weight basis.

In another embodiment, the acquisition/distribution layer comprises the stiffened fibers and up to about 25% of high surface area cellulosic material such as expanded cellulose fibers. Preferably, the acquisition/distribution layer comprising a web of wetlaid stiffened fibers and high surface area cellulose will comprise from about 85% to about 98% of the stiffened fibers, preferably from about 90% to about 95%, and from about 2% to about 15%, more preferably from about 5% to about 10%, of high surface area cellulose. The high surface area cellulosic material used herein will typically have a surface area of at least about 10 $m^2/g$, preferably at least about 20 $m^2/g$, of cellulosic material. Reference can be made to U.S. Pat. No. 4,761,203, Vinson, Aug. 2, 1988, incorporated herein by reference, for a thorough discussion of expanded cellulose fibers.

In general however, cellulosic fibers are multi-component ultrastructures made from cellulose polymers. Lignin, hemicellulose, and other components known in the art may also be present. The cellulose polymers are aggregated laterally to form threadlike structures called microfibrils. Microfibrils are reported to have diameters of about 10–20 nm, and are observable with an electron microscope. Microfibrils frequently exist in the form of small bundles known as macrofibrils. Macrofibrils can be characterized as a plurality of microfibrils which are laterally aggregated to form a threadlike structure which is larger in diameter than a microfibril, but substantially smaller than a cellulosic fiber. In general, a cellulosic fiber is made up of a relatively thin primary wall, and a relatively thick secondary wall. The primary wall, a thin, net-like covering located at the outer surface of the fiber, is principally formed from microfibrils. The bulk of the fiber wall, i.e., the secondary wall, is formed from a combination of microfibrils and macrofibrils. See *Pulp and Paper Manufacture*, Vol. 1, *Properties of Fibrous Raw Materials and Their Preparation For Pulping*, ed. by Dr. Michael Kocurek, Chapter VI, "Ultrastructure and Chemistry", pp 35–44, published jointly by Canadian Pulp and Paper Industry (Montreal) and Technical Association of the Pulp and Paper Industry (Atlanta), 3rd ed., 1983. Expanded cellulose fibers thus refers to microfibrils and macrofibrils which have been substantially separated from or disassociated from a cellulosic fiber ultrastructure.

High surface area cellulose can also be made from cellulosic fibers by passing a liquid suspension of cellulose fibers through a small diameter orifice, in which the suspension is subjected to a pressure drop of at least 3000 psig and a high velocity shearing action, followed by a high velocity decelerating impact. Passage of the suspension through the orifice is repeated until a substantially stable suspension is obtained. See U.S. Pat. No. 4,483,743, Turbak et al., Nov. 20, 1984, incorporated herein by reference.

A preferred process for preparing expanded cellulose fibers is disclosed in the Vinson patent (ibid.), and involves impacting a fibrous material having a fibrillar ultrastructure (e.g., cellulose fibers) with fine media to cause microfibrils and macrofibrils to separate from said fibrous material ultrastructure.

The length of the high surface area cellulosic material preferably ranges from about 20 to about 200 μm.

Typically, for wetlaying, the high surface area cellulose is provided as a damp pulp, generally at 15–17% solids, and preferably diluted to less than 4% solids content and processed in a beater or disc refiner to break up entanglements. The high surface area cellulose is then well mixed with the stiffened fibers in slurry and the slurry is wetlaid as described above. A blender, a deflaker or a refiner (e.g., single, cone, or double, disk refiner, or other equipment known in the art can be used to mix the stiffened fibers and high surface area cellulose. Preferably, fine mesh wires (e.g., 84H, (84×76, 5 shed weave)) are used for improved retention of the high surface are cellulose, rather than the more open wire conventionally used for the forming wire.

Other binding means for increasing physical integrity of the acquisition/distribution layer and/or facilitating processing of webs, especially wetlaid webs, for use as the acquisition/distribution layer include chemical additives, such as resinous binders, latex, and starch known in the art for providing increased integrity to fibrous webs. Suitable resinous binders include those which are known for their ability to provide wet strength in paper structures, such as can be found in TAPPI monograph series No. 29, Wet Strength, in Paper and Paperboard, Technical Association of the Pulp and Paper Industry (New York, 1965), incorporated herein by reference. Suitable resins include polyamide-epichlorohydrin and polyacrylamide resins. Other resins finding utility in this invention are urea formaldehyde and melamine formaldehyde resins. The more common functional groups of these polyfunctional resins are nitrogen containing groups such as amino groups and methylol groups attached to nitrogen. Polyethylenimine type resins may also find utility in the present invention.

Starch, particularly cationic, modified starches may also find utility as chemical additives in the present invention. Such cationic starch materials, generally modified with nitrogen containing groups such as amino groups and methylol groups attached to nitrogen, may be obtained from Natural Starch and Chemical Corporation, located in Bridgewater, N.J. Other suitable binders include, but are not limited to, polyacrylic acid polyvinyl acetate.

The level of chemical additive binders which are added will typically be from about 0.25% to about 2%, total web weight basis. Chemical additive binders which are hydrophilic, however, can be utilized in quantities. If the chemical binder additives are added to the stiffened fibers in aqueous slurry, conventionally, nonstiffened cellulosic fibers or high surface area cellulose is preferably also present, to enhance retention of the chemical additive binder. Chemical additive binders can be applied to dried or undried webs by printing, spraying, or other methods known in the art.

Thermoplastic Reinforced Acquisition/Distribution Layer

In another embodiment, the acquisition/distribution layer comprises an airlaid or wetlaid, preferably airlaid, web of stiffened cellulosic fibers wherein the web is reinforced with from about 10% to about 50%, preferably from about 25% to about 45%, more preferably from about 3.0% to about 45%, of a thermoplastic binding material, wherein the thermoplastic binding material provides bond sites at intersections of the stiffened cellulosic fibers. Such thermally bonded webs can, in general, be made by forming a web comprising the stiffened cellulosic fibers and thermoplastic fibers, which are preferably evenly distributed throughout. The web can be formed by either airlaying or wetlaying processes. Once formed, the web is thermally bonded by heating the web until the thermoplastic fibers melt. Upon melting, at least a portion of the thermoplastic material will migrate to intersections of the stiffened cellulosic fibers due to interfiber capillary gradients. These intersections become bond sites for the thermoplastic material. The web is then cooled and migrated thermoplastic material bonds the stiffened cellulosic fibers together at the bond sites. Melting and migration of the thermoplastic material to the stiffened cellulosic fiber intersections has the effect of increasing average pore size of the web, while maintaining the density and basis weight of the web as originally formed. This can improve distribution properties of the acquisition/distribution layer upon initial discharges due to improved fluid permeability, and upon subsequent discharges, due to the combined ability of the stiffened fibers to retain their stiffness upon wetting and the ability of the thermoplastic to remain bonded at the fiber intersection upon wetting and upon wet compression. In net, the thermally bonded web retains its original overall volume, but the volumetric regions previously occupied by thermoplastic fibrous material becomes open to thereby increase average interfiber capillary pore size.

Thermally bonded, thermoplastic-reinforced absorbent webs, utilizing conventional, unstiffened cellulosic fibers, are described in U.S. Pat. No. 4,590,114, D. C. Holtman, issued May 20, 1986, incorporated by reference herein and by Peter G. Bither in "Thermally Bonded Cores Add Value to Absorbent Products," Nonwovens World, November 1988, pp 49–55, both incorporated herein by reference. The processing techniques applied to make those are applicable herein.

The thermoplastic binding material should be evenly distributed throughout the web. Subsequent to formation of a dry web, the web can be heated to a temperature to melt the thermoplastic fibers but not char or otherwise damage the stiffened cellulosic fibers. Upon cooling, at least some of the resolidified thermoplastic material will provide bond sites which secure stiffened, cellulosic fibers to one another at points of individual fiber intersections to form a stabilizing network of interfiber bond sides at the intersection of the stiffened cellulosic fibers.

The thermoplastic binding materials useful for the acquisition/distribution layers herein include any thermoplastic polymer which can be melted at temperatures which will not extensively damage the cellulosic fibers. Preferably, the melting point of the thermoplastic binding material will be less than about (135° C.), preferably between about 75° C. and about 175° C. In any case, the melting point should be no lower than temperatures at which the articles of this invention are likely to be stored, whereby melting point will be typically no lower than about 50° C.

The thermoplastic binding material may, for example, be polyethylene, polypropylene, polyester, polyvinylchloride, polyvinylidene chloride. Other synthetic fibrous materials which can be utilized in thermally bonded webs are described above.

Preferably, the thermoplastic will preferably not significantly imbibe or absorb aqueous fluid. However, the surface of the thermoplastic material can be hydrophilic or hydrophobic. (As used herein, the terms "hydrophilic" and "hydrophobic" shall refer to the extent to which the surfaces are wetted by water.) The surface of the thermoplastic can be rendered hydrophilic by treatment of a hydrophobic thermoplastic binding material with a surfactant, such as a non-ionic or anionic surfactant, as by spraying the material with a surfactant or by dipping the material into the surfactant. Upon melting and resolidification, the surfactant will tend to remain at the surfaces of the thermoplastic. Suitable surfactants include non-ionic surfactants such as Brij 76 manufactured by ICI Americas, Inc. of Wilmington, Del. and the various materials sold under the Pegosperse trademark by Glyco Chemical, Inc. of Greenwich, Conn. Anionic surfactants can be also used. Surfactants are applied to the fibers at a level of from about 0.2 to about 1 gram per square meter of thermoplastic binding material. Hydrophilic materials become more desirable at higher thermoplastic material levels, particularly above about 40% of the dry web.

Thermoplastic fibers for use herein can be on the order of about 0.1 cm to about 6 cm long, preferably from about 0.3 cm to about 3.0 cm.

A preferred type of thermoplastic fibrous material is commercially known and available as PULPEX™ (Hercules, Inc., Wilmington, Del., USA). PULPEX is a polyolefin material having a very high surface area to mass ratio, which, in general, is made by spraying molten polymer and gas through a nozzle into a vacuum. PULPEX is available in both polyethylene and polypropylene forms.

The thermoplastic used can be hydrophilic or hydrophobic.

As described above, thermoplastic binder-reinforced webs of stiffened cellulosic fibers can be made by wetlaying or airlaying processes. Airlaid webs can be made by intermixing the cellulosic and thermoplastic fibers and then airlaying according to the techniques described above. The stiffened cellulosic fibers and thermoplastic fibers can be intermixed, in an airlaid context, by carding or by metering air streams of the stiffened fibers and thermoplastic fibrous material together and directing the combined system through a brush screen deposition apparatus, or other web forming device. Such techniques are known in the art. Suitable equipment includes air forming systems available from Dan Webforming International Ltd. (Risskov, Denmark). A suitable method and apparatus for mixing cellulosic and thermoplastic fibers for subsequent airlaying are also described in U.S. Pat. No. 4,590,114, Holtman, D. C., issued May 20, 1986, incorporated herein by reference. In wetlaying contexts, the thermoplastic fibrous material can be intermixed with the stiffened cellulosic fibers in the aqueous slurry prior to web formation.

The thermoplastic is preferably melted by through-air bonding, however other methods such as infra red light, etc. are not meant to be excluded. In another variation, the web is subjected to by heat embossing on one or both faces of the web. This technique is described in further detail in U.S. Pat. No. 4,590,114, which was previously incorporated into this specification.

As discussed previously, scrims such as tissue sheets and other water pervious nonwoven sheets can be used as external support in addition to or in place of the binding means described above.

Storage Layer

A second essential element of the absorbent core is a lower fluid storage layer which comprises at least 15%, by weight, preferably at least 25%, of superabsorbent material (defined more fully hereafter), and from 0% to about 85%, preferably less than about 75%, of a superabsorbent material carrier means. The principal function of the fluid storage layer is to absorb discharged body fluid from the upper acquisition/distribution layer and retain such fluid under the pressures encountered as a result of the wearer's movements. Thus, the storage layer is subjacent to and in fluid communication with the acquisition/distribution layer. Ideally the fluid storage layer will drain the upper layer of much of its acquired fluid load.

As indicated hereinbefore, the storage layer comprises superabsorbent material such as, but not necessarily limited to, discrete particles of absorbent gelling material and superabsorbent fibrous material such as acrylate grafted fibers and superabsorbent modified fibers. The superabsorbent material can be in any form which can be incorporated into a flexible web or sheet to form the storage layer. Superabsorbent materials are described in more detail below. The superabsorbent material, upon contact with fluids such as water or body fluids, absorb such fluids. (As used herein, the term "fluids" shall refer to liquids, as opposed to gases.) In this manner, fluid discharged into the acquisition/distribution layer and transported to the storage layer can be acquired and held by the superabsorbent material, thereby providing the articles herein with enhanced absorbent capacity and/or improved fluid retention performance.

The superabsorbent materials intended to be encompassed in this invention are those which are capable of absorbing at least about 10 grams, preferably at least about 15 g, more preferably at least about 20 g, of Synthetic Urine (SU—1.0% NaCl aqueous solution) per gram of superabsorbent material, as determined according to the hereinafter described Absorbent Capacity procedures.

The superabsorbent material utilized herein is typically in the form of discrete particles of absorbent gelling material. These particles will typically be distributed within a web of fibrous material as carrier means. The superabsorbent fibrous material can comprise synthetic or natural fibers. Suitable fibrous carrier means are cellulose fibers, in the form of fluff, such as is conventionally utilized in absorbent cores. Modified cellulose fibers such as the stiffened cellulose fibers described above can also be used, but are preferably not used, in the storage layer. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferred synthetic fibers have a denier of from about 3 denier per filament to about 25 denier per filament, more preferably from about 5 denier per filament to about 16 denier per filament. Also preferably, the fiber surfaces are hydrophilic or are treated to be hydrophilic.

The average dry density of the fluid storage layer comprising nonsuperabsorbent fibers as superabsorbent material carrier means will generally be in the range of from about 0.06 to about 0.5 g/cm$^3$, and more preferably within the range of from about 0.10 to about 0.4 g/cm$^3$, even more preferably from about 0.15 to about 0.3 g/cm$^3$, most preferably from about 0.15 to about 0.25 g/cm$^3$. Typically the basis weight of the lower fluid storage layer can range from about 0.02 to 0.12 g/cm$^2$, more preferably from about 0.04 to 0.08 g/cm$^2$, most preferably from about 0.05 to 0.07 g/cm$^2$.

As with the acquisition/distribution layer, density and basis weight need not be uniform throughout the storage layer. The storage layer can contain regions of relatively higher and relatively lower density and basis weight. Also as with the acquisition/distribution layer, density values for the storage layer are calculated from basis weight and layer caliper measured under a confining pressure of 0.2 psi (1.43 kPa). Density and basis weight values include the weight of the superabsorbent material. Additionally, the storage layer can have a superabsorbent material gradient, such as with more superabsorbent material being present in regions of relatively high fluid handling requirements (i.e., near the region of fluid discharge) and less superabsorbent material at lower demand regions.

The superabsorbent material which, is employed in the storage layer of the absorbent core will most often comprise a substantially water-insoluble, slightly cross-linked, partially neutralized, polymeric absorbent gelling material. This material forms a hydrogel upon contact with water. Such polymer materials can be prepared from polymerizable, unsaturated, acid-containing monomers. Suitable unsaturated acidic monomers for use in preparing the polymeric gelling material used in this invention include those listed in Brandt/Goldman/Inglin; U.S. Pat. No. 4,654,039, Issued Mar. 31, 1987, and reissued as RE 32,649 on Apr. 19, 1988, both incorporated herein by reference. Preferred monomers include acrylic acid, methacrylic acid, and 2-acrylamido-2-methyl propane sulfonic acid. Acrylic acid itself is especially preferred for preparation of the polymeric gelling agent material.

The polymeric component formed from unsaturated, acid-containing monomers may be grafted on to other types of polymer moieties such as starch or cellulose. Polyacrylate grafted starch materials of this type are also especially preferred.

Preferred polymeric absorbent gelling materials which can be prepared from conventional types of monomers include hydrolyzed acrylonitrile grafted starch, polyacrylate grafted starch, polyacrylates, maleic anhydride-based copolymers and combinations thereof. Especially preferred are the polyacrylates and polyacrylate grafted starch.

Whatever the nature of the basic polymer components of the hydrogel-forming polymeric absorbent gelling material particles used in both layers of the absorbent cores herein, such materials will in general be slightly cross-linked. Cross-linking serves to render the hydrogel-forming polymer gelling agents used in this invention substantially water-insoluble, and cross-linking thus in part determines the gel volume and extractable polymer characteristics of the hydrogels formed from the polymeric gelling agents employed. Suitable cross-linking agents are well known in the art and include, for example, those described in greater detail in Masuda et al.; U.S. Pat. No. 4,076,663; Issued Feb. 28, 1978, incorporated herein by reference. Preferred cross-linking agents are the di- or polyesters of unsaturated mono- or polycarboxylic acids with polyols, the bisacrylamides and the di- or triallyl amines. Other preferred cross-linking agents are N,N'-methylenebisacrylamide, trimethylol propane triacrylate and triallyl amine. The cross-linking agent can generally constitute from about 0.001 mole percent to 5 mole percent of the resulting hydrogel-forming polymer material. More preferably, the cross-linking agent will constitute from about 0.01 mole percent to 3 mole percent of the hydrogel-forming polymeric gelling material particles used herein.

The slightly cross-linked, hydrogel-forming polymeric gelling material particles which may be used in the articles of the present invention are generally employed in their partially neutralized form. For purposes of this invention, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to herein as the "degree of neutralization."

Webs comprising absorbent gelling material particles and nonsuperabsorbent fibrous carrier means will typically have from about 10% to about 80%, more typically from about 20% to about 75%, polymeric gelling material and from about 20% to about 90%, more typically from about 25% to about 80%, carrier means. Such webs will typically be made by airlaying, wherein an airstream of the absorbent gelling material particles is metered into an airstream of the fibrous carrier means.

It is also contemplated to provide a storage layer wherein particles of absorbent gelling material are laminated between two or more webs of fibrous material, such as exemplified in U.S. Pat. No. 4,578,068, Kramer et al., issued Mar. 25, 1986, incorporated herein by reference.

As discussed above, superabsorbent fibers can be used instead of particles of absorbent gelling material. Superabsorbent fibers have been previously disclosed in the art. Superabsorbent fibers are described in *Textile Science and Technology* Volume 7, Pronoy K. Chatterjee, editor, Elsevier Science Publishers B.V. (The Netherlands), 1985, in Chapters VII and VIII (collectively pages 217–280), incorporated by reference herein. Synthetic and modified natural fibers, such as cellulosic fibers, can be used. The superabsorbent fibers for use herein should have an absorbent capacity of at least about 10 g Synthetic Urine per g superabsorbent material (dry weight basis), preferably at least about 15 g/g.

One type of superabsorbent fiber comprise the polycarboxylate polymer-modified cellulosic fibrous pulps such as mildly hydrolyzed methyl acrylate-grafted softwood kraft pulps. These superabsorbent fibers are described in U.S. Ser. No. 07/378,154, filed Jul. 11, 1989, titled "Absorbent Paper Comprising Polymer-Modified Fibrous Pulps and Wet-Laying Process for the Production Thereof," by Larry N. Mackey and S. Ebrahim Seyed-Rezai, incorporated herein by reference.

Other types of superabsorbent fibers can include crosslinked carboxymethyl cellulose and polymer grafted cellulose fibers. Polymer grafted cellulose fibers include hydrolyzed polyacrylonitrile, polyacrylic esters, and polyacrylic and polymethacrylic acids. These superabsorbent fibers including discussion of and references to processes for making them, can be found in the Chatterjee's Vol. 7 of *Textile Science and Technology* as previously incorporated herein by reference, include: A. H. Zahran, et al., "Radiation Grafting of Acrylic and Methacrylic Acid to Cellulose Fibers to Impart High Water Sorbency", J. of App. Polymer Science, Vol. 25, 535–542 (1980), which discusses radiation grafting of methacrylic acid and acrylic acid to cellulose fibers, as the title suggests; U.S. Pat. No. 4,036,588, J. L. Williams, et al., issued Jul. 19, 1977, which describes the graft copolymerization of a vinyl monomer containing a hydrophilic group onto cellulose-containing material, e.g., rayon yarn; U.S. Pat. No. 3,838,077, H. W. Hoftiezer, et al., issued Sep. 24, 1974, which discloses polyacrylonitrile-grafted cellulose fibers.

The superabsorbent fibers can be incorporated into webs of conventional or other nonsuperabsorbent fibers, such as in wet-laid webs as described above or in air-laid webs, and can also be formed into nonwoven sheets.

In another embodiment hereof, the storage layer comprises superabsorbent fibers which are formed into nonwoven sheets. Such sheets can consist essentially of superabsorbent fibers with substantially zero percent carrier means, although such sheets can include carrier means, and such embodiments are not meant to be excluded. Nonwoven sheets made from superabsorbent fibers such as the nonacrylate superabsorbent microfibers and superabsorbent fibers useful for making such sheets are available from Arco Chemical Co. (Newtown Square, Pa., USA), under the tradename FIBERSORB™ and from Japan Exlan Co., Ltd. (Osaka, Japan) which markets superabsorbent fibers comprising a polyacrylonitrile core with a polyacrylic acid/polyammonium acrylate skin under the tradename LANSEAL™.

The storage layer embodiments of the absorbent core wherein an airlaid web comprises the carrier means can be formed by air-laying a substantially dry mixture of fibers and absorbent gelling material particles and, if desired or necessary, densifying the resulting web. Such a procedure is in general described more fully in the hereinbefore referenced Weisman and Goldman; U.S. Pat. No. 4,610,,678; Issued Sep. 9, 1986. Superabsorbent fibers can be airlaid with fibrous carrier means according to conventional airlaid web-forming processes. The superabsorbent fibers and fibrous carrier means can be blended by, for example, carding or Rando web formation.

Within the storage layer of the absorbent core, the superabsorbent material can be uniformly distributed. Alternately, there may be regions or zones of the storage layer which have higher concentrations of superabsorbent material than do other regions or zones of the layers.

As discussed above, the acquisition/distribution layer of the absorbent core preferably has a smaller surface area (in an unfolded configuration) than the storage layer and, in fact, can have a surface area that is substantially smaller than, or equal to or greater than, the fluid storage layer. Generally, the surface area of the acquisition/distribution layer will range from about 25% to about 100%, preferably from about 30% to about 95%, more preferably less than about 90%, most preferably less than about 85%, of the surface area of the storage layer.

Figure 2:
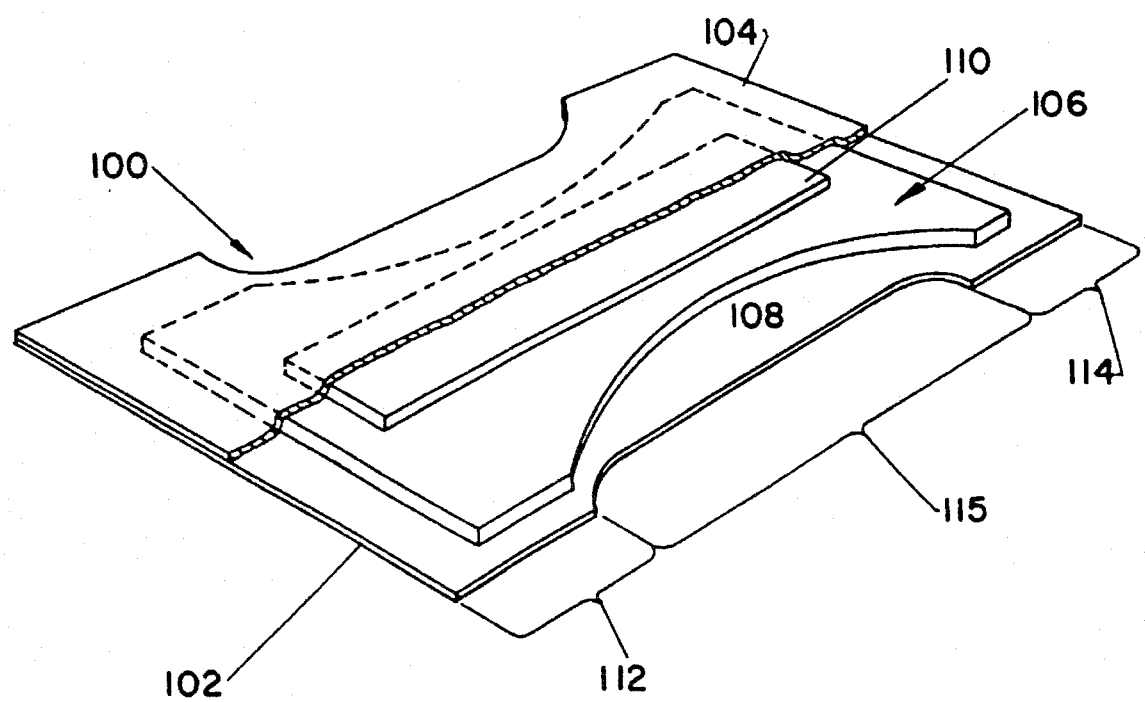
FIG. 2 represents a perspective view of a diaper structure similar to FIG. 1, but wherein the storage layer has a modified hour-glass shape.

In accordance with the present invention, the acquisition/distribution layer of the absorbent core should be placed in a specific positional relationship with respect to the topsheet and the storage layer of the absorbent article. More particularly, the acquisition/distribution layer of the core must be positioned so that it is effectively located to acquire discharged body fluid and transport said fluid to other regions of the core. Thus the acquisition/distribution layer should encompass the vicinity of the point of discharge of body fluids. These areas would include the crotch area and, preferably for males, also the region where urination discharges occur in the front of the diaper. For a diaper, the front of the absorbent articles herein means the portion of the absorbent article which is intended to be placed on the front of the wearer. Additionally, for males, it is desirable for the acquisition/distribution layer to extend to near the front waist area of the wearer to effectively acquire the relatively high fluid load that occurs in the front of the male wearer, and to compensate for directional variations of the discharges. The corresponding absorbent article regions will vary depending upon the design and fit of the absorbent article. The acquisition/distribution layers 110 of diaper 100 as shown in FIG. 2, exemplify one embodiment wherein the acquisition/distribution layer 110 is suitably positioned to receive both bowel and urine discharges for both males and females.

For disposable baby diaper executions, the acquisition/distribution layer of the core is preferably positioned relative to the elongated topsheet and/or the storage layer such that the acquisition/distribution layer is sufficiently enlongated to extend to areas corresponding at least to about 50%, preferably 75%, of the length of the storage layer. The acquisition/distribution layer should have a width sufficient to acquire gushes of body fluids without direct discharge of fluid onto the storage layer. Generally, for diapers, such as shown in FIGS. 1 and 2, the width will be at least about 5 cm, preferably at least about 6 cm. As noted, for purposes of the present invention, sections of the absorbent article can be defined by reference to top surface areas of the unfolded absorbent article found in front of a given point on the line which defines the length of the absorbent article.

For purposes of determining such acquisition/distribution layer positioning, the length of the absorbent article will be taken as the normal longest longitudinal dimension of the elongated article backing sheet. This normal longest dimension of the elongated backing sheet can be defined with respect to the article as it is applied to the wearer. When worn, the opposing ends of the back sheet are fastened together so that these joined ends form a circle around the wearer's waist. The normal length of the backing sheet will thus be the length of the line running through the back sheet from a) the point on the edge of the back sheet at the middle of the wearer's back waist, through the crotch, to b) the point on the opposite edge of the backing sheet at the middle of the wearer's front waist. The size and shape of the topsheet will generally correspond substantially to the back sheet.

In the usual instance wherein the storage layer of the absorbent core generally defines the shape of the absorbent article, the normal length of the elongated article topsheet will be approached by the longest longitudinal dimension of the storage layer of the core. However, in some applications (e.g., adult incontinence articles) wherein bulk reduction or minimum cost are important, the storage layer would not take on the general shape of the diaper or incontinence structure. Rather the storage layer would be generally located to cover only the genital region of the wearer and a reasonable area proximate to the genital area. In this instance both the fluid acquisition/distribution layer and the storage layer would be located toward the front of the article as defined by the topsheet such that the acquisition/distribution and storage layers would typically be found in the front two-thirds of the article.

The storage layer of the absorbent core can be of any desired shape consistent with comfortable fit including, for example, circular, rectangular, trapezoidal or oblong, e.g., hourglass-shaped, dog-bone-shaped, half dog bone shaped, oval or irregularly shaped. This storage layer need not be physically separated from the acquisition/distribution layer and can simply be a zone of superabsorbent material concentration in a continuous web of stiffened cellulose fiber material. More preferably, however, the storage layer of the absorbent core will comprise a separate web which can be used as an insert placed underneath the acquisition/distribution layer.

The acquisition/distribution layer can also be of any desired shape consistent with comfortable fit and the sizing limitations discussed above. These shapes include, for example, circular, rectangular, trapezoidal or oblong, e.g., hourglass-shaped, dog-bone-shaped, half dog bone shaped, oval or irregularly shaped. The acquisition/distribution layer can be of similar shape or differing shape than the storage layer.

FIGS. 1 and 2 each show diaper executions embodying the present invention. Shown in each figure is a diaper 100 with topsheet 104 and backsheet 102. Disposed between topsheet 104 and backsheet 102 is absorbent core 106 having storage layer 108 and rectangular acquisition/distribution layer 110. Although not shown, storage layer 108 has discrete particles of absorbent gelling material distributed throughout.

Specifically referring to FIG. 2, the absorbent core 106 is shown as having a front region 112, a back region 114, and a central region 115. As previously described, the front region 112, corresponds to the end of the diaper 100 that would be covering the front of the wearer when the diaper was in use, and the back region 114 would be covering the back of the user. The absorbent core 106 of FIG. 2, specifically the storage layer 108, has a modified hour-glass shape to provide enhanced fit and reduce in-use leakage.

Figure 3:
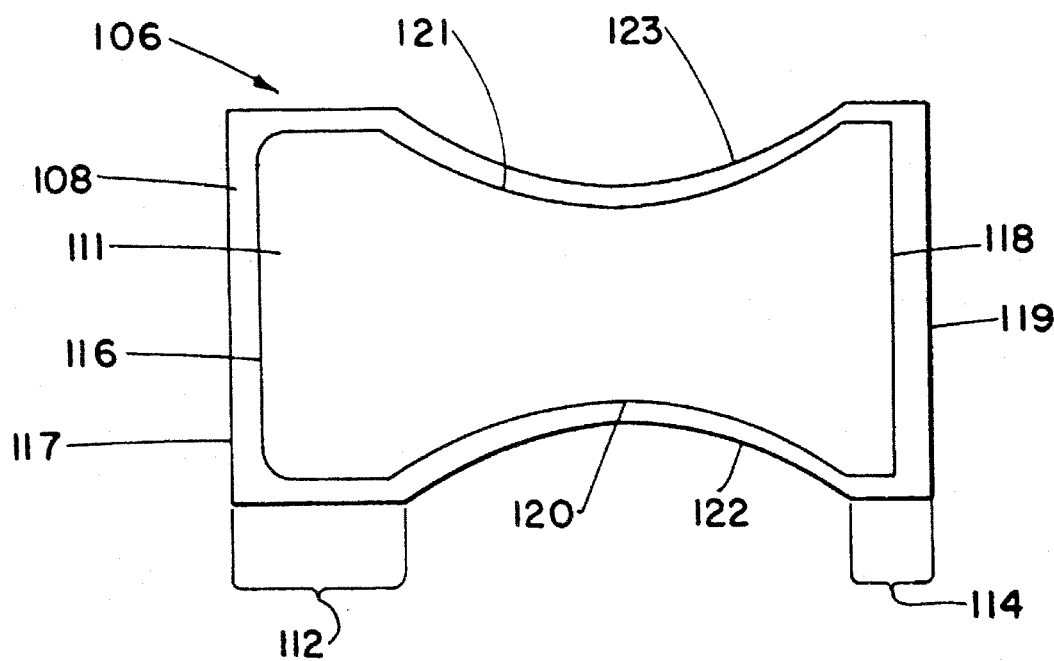
FIG. 3 represents a direct view of an absorbent core useful for diaper applications, such as in FIGS. 1 and 2, wherein the core has a modified hour glass-shaped storage core and a similar hour glass-shaped acquisition/distribution layer.

FIG. 3 shows an absorbent core 106, that can be utilized in conjunction with a disposable diaper, having a storage layer 108 of similar shape to those of FIGS. 1 and 2. Acquisition/distribution layer 111, however, is of a modified hour-glass shape of substantially similar shape to the storage layer 108, though of smaller surface area.

Further with respect to FIG. 3, the absorbent core 106 has front region 112, rear region 114, and central region 115. Front region 112, front edge 117 and, at rear region 114, has rear edge 119. Front edge 117 and, has rear edge 119. Front edge 117 and rear edge 119 are connected by storage layer side edges 122 and 123, corresponding to the central region 115. Acquisition/distribution layer 111 has front edge 116 in the front region 112 and rear edge 118 in the rear region 114. Acquisition/distribution layer side edges 120 and 121, connect front edge 116 and rear edge 118.

In preferred absorbent article embodiments, e.g., disposable absorbent diapers, the edges 116, 118, 120, 121 of the acquisition/distribution layer 111 will respectively be at least 0.5 cm., preferably at least 1.25 cm. inside the edges 117, 119, 122, 123 of the storage layer 108, particularly in central region 115.

Superabsorbent Material Absorbent Capacity Test Method

As discussed above, the superabsorbent materials for use in the present invention will preferably have an Absorbent Capacity of at least about 10 g, preferably at least about 15 g, more preferably at least about 20 g Synthetic Urine (1.0% NaCl aqueous solution, prepared using distilled water) per gram dry superabsorbent material. In general, the superabsorbent material is place within a tea bag, immersed in an excess of Synthetic Urine for a specified time, and then centrifuged for a specified period of time. The ratio of superabsorbent material final weight after centrifuging minus initial weight to initial weight is Absorbent Capacity.

The following procedure can be used to determine Absorbent Capacity. The procedure is conducted under standard laboratory conditions.

Using a 6 cm×12 cm cutting die, the tea bag material is cut, folded in half lengthwise, and sealed along two sides with a T-bar heat sealer to produce a 6 centimeter by 6 centimeter tea bag square. The tea bag material utilized is grade 1234 heat sealable, obtainable from C. H. Dexter, Division of the Dexter Corp., Windsor Locks, Conn., USA, or equivalent. Lower porosity tea bag material should be used if required to retain fine superabsorbent materials. 0.200 grams plus or minus 0.005 grams of superabsorbent material is weighed onto a weighing paper and transferred into the tea bag, and the top (open end) of the tea bag is sealed. An empty tea bag is sealed at the top and is used as a blank. Approximately 400 milliliters of Synthetic Urine are poured into a 1,000 milliliter beaker. The blank tea bag is submerged in the Synthetic Urine. The tea bag containing the superabsorbent material (the sample tea bag) is held horizontally to distribute the material evenly throughout the tea bag. The tea bag is laid on the surface of the Synthetic Urine. The tea bag is allowed to wet, for a period of no more than one minute, and then submerged and soaked for 60 minutes. Approximately 2 minutes after the first sample is submerged, a second set of tea bags, prepared identically to the first set of blank and superabsorbent material-containing tea bags, is submerged and soaked for 60 minutes in the same manner as the first set. After the prescribed soak time is elapsed, for each set of tea bag samples, the tea bags are promptly removed (with tongs) from the Synthetic Urine. The samples are then centrifuged as described below. The centrifuge used is a Delux Dynac II Centrifuge, Fisher Model No. 05-100-26, obtainable from Fisher Scientific (Pittsburgh, Pa., USA), or equivalent. The centrifuge should be equipped with a direct read tachometer and an electric brake. The centrifuge is further equipped with a cylindrical insert basket having an approximately 2.5 inch (6.35 cm) high outer wall with an 8.435 inch (21.425 cm) outer diameter, an 7.935 inch (20.155 cm) inside diameter, and 9 rows each of approximately 106³⁄₃₂ inch (0.238 cm) diameter circular holes equally spaced around the circumference of the outer wall, and having a basket floor with six ¼ inch (0.635 cm) diameter circular drainage holes equally spaced around the circumference of the basket floor at a distance of ½ inch (1.27 cm) from the interior surface of the outer wall to the center of the drainage holes, or equivalent. The basket is mounted in the centrifuge so as to rotate, as well as brake, in unison with the centrifuge. The superabsorbent material-containing tea bags are positioned in the centrifuge basket with a folded end of the tea bag in the direction of centrifuge spin. The blank tea bags are placed to either side of the corresponding sample tea bags. The superabsorbent material-containing tea bag from the second set of tea bags must be placed opposite the superabsorbent material-containing tea bags from the first set of tea bags; and the second blank tea bag, opposite the first blank, to balance the centrifuge. The centrifuge is started and allowed to ramp up quickly to a stable 1,500 rpm. Once the centrifuge has been stabilized at 1,500 rpm, a timer is set for 3 minutes. After 3 minutes, the centrifuge is turned off and the brake is applied. The first superabsorbent material-containing tea bag and first blank tea bag are removed and weighed separately. The procedure is repeated for the second set of tea bags. The absorbent capacity (ac) for each of the samples is calculated as follows: ac=(Superabsorbent material-containing tea bag weight after centrifuge minus blank tea bag weight after centrifuge minus dry superabsorbent material weight) divided by (dry superabsorbent material weight). The Absorbent Capacity value for use herein is the average absorbent capacity (ac) of the two samples.

EXAMPLE I

A disposable diaper is prepared comprising a thermally bonded polypropylene topsheet, a fluid impervious polyethylene backing sheet and a dual layer absorbent core positioned between the topsheet and the backing sheet. The dual layer absorbent core comprises an hourglass-shaped storage layer positioned below a rectangular shaped acquisition/distribution layer, as shown in FIG. 1.

The acquisition/distribution layer comprises stiffened, twisted, curled cellulose fibers and optionally a binding means. The storage layer comprises an air-laid mixture of conventional cellulosic fluff (Foley fluff, southern softwood kraft pulp, The Procter & Gamble Cellulose Co., Memphis, Tenn., USA) and sodium polyacrylate polymeric absorbent gelling material of the type described in RE U.S. Pat. No. 32,649, reissued Apr. 19, 1988, and having an Absorbent Capacity of about 30 g/g. The acquisition/distribution layer comprises a 92%/8% wetlaid mixture of stiffened fibers and conventional nonstiffened cellulosic fibers. The nonstiffened fibers are also made from Foley Fluff; and are refined to about 200 CSF. The stiffened, twisted, curled cellulosic fibers are made from southern softwood kraft pulp (Foley fluff) and crosslinked with glutaraldehyde to the extent of about 2.5 mole percent on a dry fiber cellulose anhydroglucose basis. The fibers are crosslinked according to the "dry crosslinking process" as described above in U.S. Pat. No. 4,822,453.

The stiffened fibers are similar to the fibers having the characteristics described in Table 1.

TABLE 1

Stiffened, Twisted, Curled Cellulose (STCC) Fibers

Type=Southern softwood kraft pulp crosslinked with glutaraldehyde to the extent of mole percent on a dry fiber cellulose anhydroglucose basis Twist Count Dry=6.8 nodes/m Twist Count Wet=5.1 nodes/mm Isopropol Alcohol Retention Value=24%

Water Retention Value=37%

Curl Factor=0.63

The acquisition/distribution layer is a uniform, wetlaid web as described in Example II. The acquisition/distribution layer has an average dry density of about 0.06 g/cc. An average density upon saturation with Synthetic Urine, dry weight basis, of about 0.07 g/cc, and an average basis weight of about 0.03 g/cm². The storage layer comprises 50% by weight Foley fluff and 50% absorbent gelling material particles, has an average dry density of about 0.24 g/cc and an average dry basis weight of about 0.5 g/cm².

The acquisition/distribution layer has dimensions of about 7.6 cm×22.9 cm and is positioned relative to the storage layer as shown in FIG. 1. The storage layer has crotch width (at the most narrow part of the crotch) of about 8.9 cm, a width at the front waist area of about 21.6 cm, and a width at the rear (back) waist area of about 16.5 cm.

In an alternative embodiment, the, storage layer comprises about 15% of the absorbent gelling material particles and about 85% of Foley fluff and has a basis weight gradient such that the front 60% of the storage core has a basis weight of about 0.11 g/cm² and a density of about 0.15 g/cc and the rear 40% of the storage core has a basis weight of about 0.04 g/cm² and a density of about 0.06 g/cc.

In a further embodiment, the storage core comprises about 28% of the absorbent gelling material particles and about 72% of Foley fluff, and has basis weight and density gradients as described immediately above.

EXAMPLE II

This example exemplifies wetlaying of a web useful for use as an acquisition/distribution layer in the present invention. The web comprises 92% stiffened fibers, as described in Example I and Table I, and 8% highly refined Foley fluff (crill) having a freeness of about 200 CSF.

A pulp slurry of the stiffened and nonstiffened fibers having a fiber consistency of 0.1–0.2% is pumped to a FORMAR papermaking machine at a linear velocity of 25 m/s and at rate of about 95 liters/minute. The slurry is distributed by a fixed-roof former headbox onto an inch wide (30.5 cm) 84M, 5 shed 12 forming wire moving continuously at a rate of 1.5 m/minutes. Linear velocity of the pulp slurry upon exit from the headbox is from 50 to 100 m/s. Flow and wire movement are regulated so that a uniform, moist sheet having a dry basis weight of about 0.03 g/cm² and an average dry density of about 0.06 g/cc is formed. Sheet consistency is increased to about 16%–22% by application of two vacuum boxes from underneath the wire, such vacuum boxes operating in sequence at 75 mm Hg and 100 mm Hg, respectively, with a residence time for the sheet being subject to each vacuum box of about 1 second. The sheet is then removed from the forming wire manually and dried, batchwise, in a forced convection steam heated oven for about 4 hours at about 110° C.

EXAMPLE III

Absorbent cores are prepared as in Example I, except that the acquisition/distribution layer is airlaid and comprises 100% of the stiffened fibers.

EXAMPLE IV

Absorbent cores are prepared as in Example III except that the acquisition/distribution layer is made from an airlaid and thermally bonded thermoplastic-reinforced web comprising 55% of the stiffened fibers and 45% of PULPEX™ (Hercules, Inc., Wilmington, Del., USA) polyethylene microfibers having an average length of about 0.3 cm. The acquisition/distribution layer is formed by metering airstreams of the stiffened fibers and PULPEX, and then forming the web using conventional airlaying equipment. The web is thermally bonded by heating the web by through-air bonding, under unrestrained (i.e., uncompressed) conditions, and subsequently allowed to cool.

What is claimed is:

1. An absorbent article for acquisition, distribution, and storage of bodily fluids, said article comprising:
   (a) a fluid pervious topsheet;
   (b) a fluid impervious backsheet affixed to said top sheet; and
   (c) an absorbent core disposed between said topsheet and said backsheet, said absorbent core having:
      (i) a thermally bonded hydrophilic fluid acquisition/ distribution layer having an average dry density of less than 0.30 g/cc and an average dry basis weight of from about 0.001 to about 0.10 g/cm², said acquisition/distribution layer comprising a web of from about 50% to 90%, dry weight basis, hydrophilic chemically stiffened cellulosic fibers and from about 10% to about 50%, dry weight basis, of a thermoplastic bonding material forming bond sites at intersections of said hydrophilic stiffened fibers; said acquisition/distribution layer having been made by preparing a web of a blend of said hydrophilic stiffened fibers and from about 10% to about 50%, by weight of the dry web, of thermoplastic fibrous material, heating the web to melt the thermoplastic fibrous material to provide said thermoplastic bonding material, and cooling the web, whereby said thermoplastic bonding material, upon melting and subsequent cooling, migrates to and forms said bond sites at said intersections of said hydrophilic stiffened cellulosic fibers; and (ii) a fluid storage layer, positioned beneath said acquisition/distribution layer relative to said topsheet, comprising at least about 15%, by weight of said storage layer, of superabsorbent material and from 0% to about 85% of a carrier means for said superabsorbent material;

said acquisition/distribution layer having a top surface area which is at least about 15% of the top surface area of said fluid storage layer.

2. An absorbent article as in claim 1, wherein said acquisition/distribution layer has a top surface area which is from about 25% to about 100% of the top surface area of said storage layer, and said fluid acquisition/distribution layer contains no more than about 6.0%, by weight, superabsorbent material.

3. An absorbent article, as in claim 2, wherein said acquisition/distribution layer has an average dry density that is between about 0.02 g/cc to about 0.20 g/co and an average dry basis weight of between about 0.01 g/cm$^2$ and about 0.08 g/cm$^2$.

4. An absorbent article as in claim 2, wherein said acquisition/distribution layer has a top surface area which is from about 30% to about 95% of the top surface area of said storage layer, and said acquisition/distribution layer is substantially free of superabsorbent material.

5. An absorbent article, as in claim 4, wherein said carrier means of said storage layer comprises a web of cellulosic fibers and said superabsorbent material of said storage layer comprises discrete particles of absorbent gelling material.

6. An absorbent article, as in claim 5, wherein said storage layer comprises from about 25% of said superabsorbent material.

7. An absorbent article, as in claim 4, wherein said acquisition/distribution layer comprises from about 25% to about 45% of said thermoplastic bonding material.

8. An absorbent article, as in claim 7, wherein said acquisition/distribution layer comprises from about 30% to about 45% of said thermoplastic bonding material.

9. An absorbent article, as in claim 7, wherein said carrier means for said superabsorbent material comprises a web of cellulosic fibers, and wherein said storage layer comprises from about 20% to about 75% of said superabsorbent material.

10. An absorbent article, as in claim 7, wherein said acquisition/distribution layer has an average dry density that is between about 0.02 g/cc to about 0.20 g/cc and an average dry basis weight of between about 0.01 g/cm$^2$ and about 0.08 g/cm$^2$.

11. An absorbent article as in claim 10, wherein said acquisition/distribution layer has an average dry basis of from about 0.05 g/cc to about 0.15 g/cc and an average dry basis weight of from about 0.015 g/cm$^2$ to about 0.04 g/cm$^2$.

12. An absorbent structure comprising a thermally bonded hydrophilic fluid acquisition/distribution layer having an average dry density of less than 0.30 g/cc and an average dry basis weight of from about 0.001 to about 0.10 g/cm$^2$, said acquisition/distribution layer comprising a web of from about 50% to 90%, dry weight basis, chemically stiffened cellulosic fibers and from about 10% to about 50%, dry weight basis, of a thermoplastic bonding material forming bond sites at intersections of said hydrophilic stiffened fibers; said acquisition/distribution layer having been made by preparing a web of a blend of said hydrophilic stiffened fibers and from about 10% to about 50%, by weight of the dry web, of thermoplastic fibrous material, heating the web to melt the thermoplastic fibrous material to provide said thermoplastic bonding material, and cooling the web, whereby said thermoplastic bonding material, upon melting and subsequent cooling, migrates to and forms said bond sites at said intersections of said hydrophilic stiffened fibers.

13. An absorbent structure, as in claim 12, wherein said acquisition/distribution layer comprises from about 25% to about 45% of said thermoplastic bonding material.

14. An absorbent structure, as in claim 13, wherein said acquisition/distribution layer comprises from about 30% to about 45% of said thermoplastic bonding material.

15. An absorbent structure for acquisition, distribution, and storage of bodily fluids, said structure comprising:

(i) a thermally bonded hydrophilic fluid acquisition/distribution layer having an average dry density of less than 0.30 g/cc and an average dry basis weight of from about 0.001 to about 0.10 g/cm$^2$, said acquisition/distribution layer comprising a web of from about 50% to 90%, dry weight basis, hydrophilic chemically stiffened cellulosic fibers and from about 10% to about 50%, dry weight basis, of a thermoplastic bonding material forming bond sites at intersections of said hydrophilic stiffened fibers; said acquisition/distribution layer having been made by preparing a web of a blend of said hydrophilic stiffened fibers and from about 10% to about 50%, by weight of the dry web, of thermoplastic fibrous material, heating the web to melt the thermoplastic fibrous material to provide said thermoplastic bonding material, and cooling the web, whereby said thermoplastic bonding material, upon melting and subsequent cooling, migrates to and forms said bond sites at said intersections of said hydrophilic stiffened fibers; and (ii) a fluid storage layer, positioned beneath said acquisition/distribution layer, comprising at least about 15%, by weight of said storage layer, of superabsorbent material and from 0% to about 85% of a carrier means for said superabsorbent material;

said acquisition/distribution layer having a top surface area which is at least about 15% of the top surface area of said fluid storage layer.

16. An absorbent structure as in claim 15, wherein said fluid acquisition/distribution layer has a top surface area which is from about 25% to about 100% of the top surface area of said storage layer, and said fluid acquisition/distribution layer is substantially free of superabsorbent material.

17. An absorbent structure, as in claim 16, wherein said acquisition/distribution layer has an average dry density that is between about 0.02 g/cc and about 0.20 g/cc and an average dry basis weight of between about 0.01 g/cm$^2$ and about 0.08 g/cm$^2$.

18. An absorbent structure as in claim 16, wherein said fluid acquisition/distribution layer has a top surface area which is from about 30% to about 95% of the top surface area of said storage layer.

19. An absorbent structure, as in claim 18, wherein said carrier means of said storage layer comprises a web of cellulosic fibers and wherein said superabsorbent material of said storage layer comprises discrete particles of absorbent gelling material.

20. An absorbent structure, as in claim 19, wherein said storage layer comprises at least about 25% of said superabsorbent material.

21. An absorbent structure, as in claim 18, wherein said acquisition/distribution layer comprises from about 25% to about 45% of said thermoplastic bonding material.

22. An absorbent structure, as in claim 21, wherein said acquisition/distribution layer comprises from about 30% to about 45% of said thermoplastic bonding material.

23. An absorbent structure, as in claim 21, wherein said carrier means for said superabsorbent material comprises a web of cellulosic fibers, and said storage layer comprises from about 25% to about 75% of said superabsorbent material.

24. An absorbent structure, as in claim 21, wherein said acquisition/distribution layer has an average dry density that is between about 0.02 g/cc and about 0.20 g/cc and an average dry basis weight of between about 0.01 g/cm$^2$ and about 0.08 g/cm$^2$.

25. An absorbent structure, as in claim 24, wherein said acquisition/distribution layer has an average dry density of from about 0.05 g/cc to about 0.05 g/cc and an average dry basis weight of from about 0.015 g/cm$^2$ to about 0.04 g/cm$^2$.

* * * * *

UNITED STATES PATENT AND TRADEMARK OFFICE
CERTIFICATE OF CORRECTION

PATENT NO. : 5,531,728
DATED : July 2, 1996
INVENTOR(S) : Glen R. Lash

It is certified that error appears in the above-identified patent and that said Letters Patent is hereby corrected as shown below:

In Col. 5, line 38, "Joined" should read --joined--.

In Col. 9, line 17, "fiber's" should read --fibers--.

In Col. 12, line 8, "blinding" should read --binding--.

In Col. 13, line 43, "web," should read --web--.

In Col. 15, line 40, "84H," should read --84M,--.

In Col. 16, line 18, "3.0%" should read --30%--.

In Col. 21, line 38, "4,610,,678" should read --4,610,678--.

In Col. 27, line 35, "0.20 g/co" should read --0.20 g/cc--.

Signed and Sealed this

Twentieth Day of May, 1997

*Attest:*

BRUCE LEHMAN

*Attesting Officer*     *Commissioner of Patents and Trademarks*